United States Patent [19]

Müller et al.

[11] Patent Number: 4,804,655
[45] Date of Patent: Feb. 14, 1989

[54] PESTICIDAL CYCLIC MALONYLPHOSPHONIC DIAMIDES

[75] Inventors: Nikolaus Müller, Monheim; Gerhard Bonse, Cologne; Peter Andrews; Wilhelm Stendel, both of Wuppertal; Robert Steffens, Cologne, all of Fed. Rep. of Germany

[73] Assignee: Bayer Aktiengesellschaft, Leverkusen, Fed. Rep. of Germany

[21] Appl. No.: 945,442

[22] Filed: Dec. 22, 1986

[30] Foreign Application Priority Data

Jan. 8, 1986 [DE] Fed. Rep. of Germany ....... 3600289

[51] Int. Cl.$^4$ .................. A01N 57/36; C07F 9/22
[52] U.S. Cl. ..................... 514/100; 514/105; 260/505 R; 558/231; 564/13; 549/220
[58] Field of Search ............... 564/13; 514/105, 100; 260/505 R; 541/220, 231

[56] References Cited

FOREIGN PATENT DOCUMENTS 643563 6/1984 Switzerland .

Primary Examiner—Anton H. Sutto
Attorney, Agent, or Firm—Sprung Horn Kramer & Woods

[57] ABSTRACT

Novel pesticidally active cyclic malonylphosphonic diamides of the formula

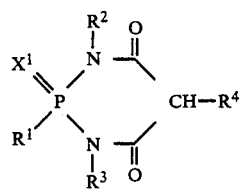

in which
X represents O or S,
$R^1$ represents alkyl, alkenyl, alkinyl, cycloalkyl, aryl or heteroaryl, each of which can be optionally substituted,
$R^2$ represents hydrogen, alkyl, aryl or aralkyl,
$R^3$ represents hydrogen, alkyl, aryl or aralkyl, and
$R^4$ represents an acyl radical,
or salts thereof, Many intermediates are new, 11 Claims, No Drawings

PESTICIDAL CYCLIC MALONYLPHOSPHONIC DIAMIDES

The present invention relates to novel cyclic malonylphosphonic diamides, processes for their preparation, and their use as pesticides in agriculture, forestry and in the household, hygiene, stored goods and material protection and veterinary medicine areas.

Phenylcarbamoyl-substituted diazaphosphorines have already been disclosed. They are suitable as pesticides and also as ectoparasiticides (CH-PS (Swiss Patent Specification) No. 643,563). However, their action, above all at low application concentrations, is not always completely satisfactory.

1. The novel cyclic malonylphosphonic diamides of the formula I,

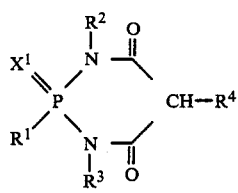

in which
$X^1$ represents O or S
$R^1$ represents alkyl, alkenyl, alkinyl, cycloalkyl, aryl or heteroaryl, each of which can be optionally substituted,
$R^2$ represents hydrogen, alkyl, aryl or aralkyl,
$R^3$ represents hydrogen, alkyl, aryl or aralkyl,
$R^4$ represents acyl radicals, have been found.

The compounds of the formula I can be present in the form of their various tautomers (keto/enol) and as mixtures of these tautomers, and also in the form of their salts with bases.

2. It has been found that the compounds of the formula I

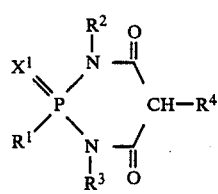

in which
$X^1$ represents O or S,
$R^1$ represents alkyl, alkenyl, alkinyl, cycloalkyl, aryl, aralkyl or heteroaryl, each of which can be optionally substituted,
$R^2$ represents hydrogen, alkyl, aryl or aralkyl,
$R^3$ represents hydrogen, alkyl, aryl or aralkyl,
$R^4$ represents acyl radicals,
are obtained by reacting diazaphosphorines of the formula II

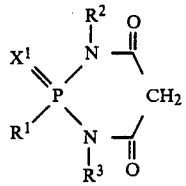

in which
$X^1$, $R^1$, $R^2$, $R^3$ have the abovementioned meaning,
(a) with isocyanates of the formula III $$R^5-NCO(S) \quad\quad III$$

in which
$R^5$ represents optionally substituted alkyl, aryl or acyl,
if appropriate in the presence of catalysts, or
(b) with compounds of the formula IV $$R^6-X^2 \quad\quad IV$$

in which
$X^2$ represents the radicals —CO(S)Hal, —CO—O—CO—$R^6$,
$R^6$ represents optionally substituted alkyl, aryl or the —O—$R^7$ or —$NR^8R^9$ radicals,
$R^7$ represents alkyl or aryl,
$R^8$ represents hydrogen, optionally substituted alkyl, aryl or acyl,
$R^9$ represents hydrogen optionally substituted alkyl or aryl,
$R^8$ and $R^9$, together with the neighboring nitrogen atom, represent a saturated heterocycle which optionally contains further heteroatoms and which can be optionally substituted
in the presence of acid acceptors, or by rearranging
(c) compounds of the formula V

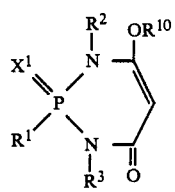

in which
$X^1$, $R^1$, $R^2$, $R^3$ have the abovementioned meaings,
$R^{10}$ represents the —CO(S)$R^6$ radical,
where
$R^6$ has the abovementioned meaning, in the presence of strong bases, or by reacting
(d) compounds of the formula VI

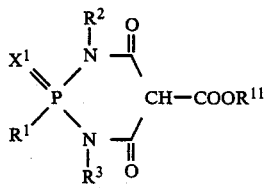

in which
$X^1$, $R^1$, $R^2$ and $R^3$ have the abovementioned meaning and $R^{11}$ represents $C_{1-4}$-alkyl or phenyl which is optionally substituted by $NO_2$, with amines of the formula VII $$HNR^8R^9 \qquad VII$$

in which $R^8$ and $R^9$ have the abovementioned meaning.

3. The compounds of the formula II

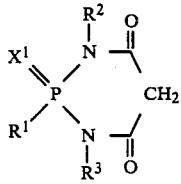

in which $X^1$, $R^1$, $R^2$, $R^3$ have the abovementioned meaning, are novel.

4. The compounds of the formula II

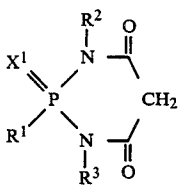

in which $X^1$, $R^1$, $R^2$, $R^3$ have the abovementioned meaning, are obtained by reacting compounds of the formula VIII

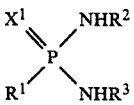

in which $X^1$, $R^1$, $R^2$, $R^3$ have the above indicated meaning with compounds of the formula IX $$CH_2(COR^{12})_2 \qquad IX$$

in which $R^{12}$ represents halogen, OH, $C_{1-4}$-alkoxy or phenoxy.

The compounds of the formula V

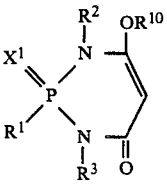

in which $X^1$, $R^1$, $R^2$, $R^3$, $R^{10}$ have the abovementioned meaning, are novel.

6. The compounds of the formula V

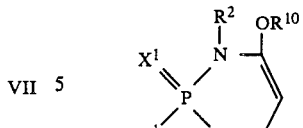

in which $X^1$, $R^1$, $R^2$, $R^3$, $R^{10}$ have the abovementioned meaning, are obtained by reacting compounds of the formula II

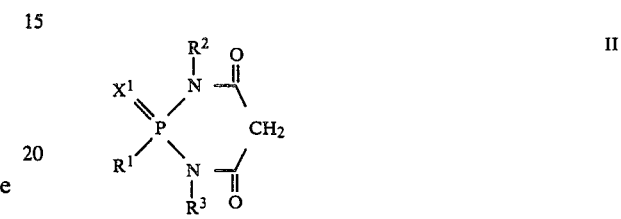

in which $X^1$, $R^1$, $R^2$, $R^3$ have the abovementioned meaning, with compounds of the formula IV $$R^6\text{—}X^2 \qquad IV$$

in which $R^6$ and $R^7$ have the abovementioned (point 2b) meaning.

The compounds of the formula I can be employed to excellent effect as pesticides, particularly as insecticides, fungicides and acaricides in the agricultural and forestry, household, hygiene, stored goods and material protection areas, and also as ecto- and endoparasiticides in the veterinary medicine area.

Preferred compounds of the formula I are those in which $X^1$ represents O or S, particularly O, $R^1$ represents $C_{1-20}$-alkyl, $C_{2-20}$-alkenyl, $C_{2-20}$-alkinyl, $C_{3-10}$-cycloalkyl, phenyl, naphthyl, heteroaryl having up to 7 ring atoms and N, O, S as heteroatoms, each of which can be optionally substituted by one or more of the following radicals: alkyl having preferbly 1 to 4, particularly 1 or 2, carbon atoms, such as methyl, ethyl, n.- and i.-propyl and n.-, i.-, s.- and t.-butyl; alkoxy having preferably 1 to 4, particularly 1 or 2, carbon atoms, such as methoxy, ethoxy, n.- and i.-propyloxy and n.-, i.-, s.- and t.-butyloxy; alkylthio having preferably 1 to 4, particularly 1 or 2, carbon atoms, such as methylthio, ethylthio, n.- and i.-propylthio and n.-, i.-, s.- and t.-butylthio; haloalkyl having preferably 1 t 4, particularly 1 or 2, carbon atoms and preferably 1 to 5, particularly 1 to 3, halogen atoms, the halogen atoms being identical or different and fluorine, chlorine or bromine, particularly fluorine, preferably representing halogen atoms, such as trifluoromethyl, fluoro-, chloroethyl; haloalkoxy having preferably 1 to 4, particularly 1 to 2, carbon atoms and preferably 1 to 5, particularly 1 to 3, halogen atoms, the halogen atoms being identical or different and fluorine, chlorine, bromine, particularly fluorine, preferably representing halogen atoms, such as trifluoromethoxy; haloalkylthio having preferably 1 to 4, particularly 1 or 2, carbon atoms and preferably 1 to 5, particularly 1 to 3, halogen atoms, the halogen atoms being identical or different and fluorine, chlorine, bromine, particularly fluorine, preferably representing halogen atoms, such as trifluoromethylthio; alkylenedioxy having preferably 1 or 2 carbon atoms, such as methylenedioxy or ethylenedioxy; halo-substituted alkylenedioxy having preferably 1 or 2 carbon atoms and preferably 1 to 4, particularly 2 to 3, halogen atoms, the halogen atoms being identical or different and fluorine or chlorine, particularly fluorine, preferably representing halogen atoms, such as difluoromethylenedioxy, trifluoroethylenedioxy, tetrafluoroethylenedioxy; hydroxy; halogen, preferably fluorine, chlorine, bromine and iodine, particularly chlorine and bromine; cyano; nitro; amino; monoalkyl- and dialkylamino having preferably 1 to 4, particularly 1 or 2, carbon atoms per alkyl group, such as methylamino, methyl- ethylamino, n.- and i.-propylamino and methyl-n.-butylamino; formyl; carboxyl; alkylcarbonyl having preferably 2-4 carbon atoms; carbalkoxy having preferably 2 to 4, particularly 2 or 3, carbon atoms, such as carbomethoxy and carboethoxy; sulpho (—SO₃H); alkylsulphonyl having preferably 1 to 4, particularly 1 or 2, carbon atoms, such as methylsulphonyl and ethylsulphonyl; arylsulphonyl having preferably 6 or 10 aryl carbon atoms, such as phenylsulphonyl; phenyl, naphthyl, phenoxy, naphthoxy, phenylthio, naphthylthio, which themselves can again be substituted $R^2$ represents hydrogen, $C_1$-$C_4$-alkyl, phenyl, benzyl, each of which can be optionally substituted, $R^3$ represents hydrogen, $C_1$-$C_4$-alkyl, phenyl, benzyl, each of which can optionally be substituted, $R^4$ represents the —CO(S)$R^6$ radical, $R^6$ represent straight-chain, branched or cyclic alkyl having up to 20 C atoms, which is optionally substituted by halogen, particularly chlorine, fluorine, bromine, $C_1$-$C_4$-alkoxy, particularly methoxy, ethoxy, furthermore phenyl which is optionally substituted by alkyl having preferably 1 to 4, particularly 1 or 2, carbon atoms, such as methyl, ethyl, n.- and i.-propyl and n.-, i.- and t.-butyl; alkoxy having preferably 1 to 4, particularly 1 or 2, carbon atoms, such as methoxy, ethoxy, n.- and i.-propyloxy and n.-, i.- and t.-butyloxy; alkylthio having preferably 1 to 4, particularly 1 to 2, carbon atoms, such as methylthio, ethylthio, n.- and i.-propylthio and n.-, i.-, s.- and t.-butylthio; haloalkyl having preferably 1 to 4, particularly 1 or 2, carbon atoms and preferably 1 to 5, particularly 1 to 3, halogen atoms, the halogen atoms being identical or different and fluorine, chlorine or bromine, particularly fluorine, preferably representing halogen atoms, such as trifluoromethyl, fluoro-chloroethyl; haloalkoxy having preferably 1 to 4, particularly 1 or 2, carbon atoms and preferably 1 to 5, particularly 1 to 3, halogen atoms, the halogen atoms being identical or different and fluorine, chlorine, bromine, particularly fluorine, preferably representing halogen atoms, such as trifluoromethoxy; haloalkylthio having preferably 1 to 4, particularly 1 or 2, carbon atoms and preferably 1 to 5, particularly 1 to 3, halogen atoms, the halogen atoms being identical or different and fluorine, chlorine, bromine, particularly fluorine, preferably representing halogen atoms, such as trifluoromethylthio; alkylenedioxy having preferably 1 or 2 carbon atoms, such as methylenedioxy or ethylenedioxy; halo-substituted alkylenedioxy having preferably 1 or 2 carbon atoms and preferably 1 to 4, particularly 2 to 3, halogen atoms, the halogen atoms being identical or different and fluorine or chlorine, particularly fluorine, preferably representing halogen atoms, such as difluoromethylenedioxy, trifluoroethylenedioxy, tetrafluoroethylenedioxy; hydroxy; halogen, preferably fluorine, chlorine, bromine and iodine, particularly chlorine and bromine; cyano; nitro; amino; monoalkyl- and dialkylamino having preferably 1 to 4, particularly 1 or 2, carbon atoms per alkyl group, such as methylamino, methyl-ethyl-amino, n.- and i.-propylamino and methyl-n.-butylamino; formyl; carboxy; alkylcarbonyl having preferably 2-4 carbon atoms; carbalkoxy having preferably 2 to 4, particularly 2 or 3, carbon atoms, such as carbomethoxy and carboethoxy; sulpho (—SO₃H); alkylsulphonyl having preferably 1 to 4, particularly 1 or 2, carbon atoms, such as methylsulphonyl and ethylsulphonyl; arylsulphonyl having preferably 6 or 10 aryl carbon atoms, such as phenylsulphonyl; phenyl, naphthyl, phenoxy, naphthoxy, phenylthio, naphthylthio, which themselves can again be substituted.

$R^6$, further, preferably represents the —O—$R^7$ and —N$R^8R^9$ radicals, where $R^8$ preferably represents hydrogen, $C_{1-4}$-alkyl, $R^9$ preferably represents hydrogen, $C_{1-4}$-alkyl, phenyl, which is optionally substituted by alkyl having preferably 1 to 4, particularly 1 or 2, carbon atoms, such as methyl, ethyl, n.- and i.-propyl and n.-, i.-, s.- and t.-butyl; alkoxy having preferably 1 to 4, particularly 1 or 2, carbon atoms, such as methoxy, ethoxy, n.- and i.-propyloxy and n.-, i.-, s.- and t.-butyloxy; alkylthio having preferably 1 to 4, particularly 1 or 2, carbon atoms, such as methylthio, ethylthio, n.- and i.-propylthio and n.-, i.-, s.- and t.-butylthio; haloalkyl having preferably 1 to 4, particularly 1 or 2, carbon atoms and preferably 1 to 5, particularly 1 to 3, halogen atoms, the halogen atoms being identical or different and fluorine, chlorine or bromine, particularly fluorine, preferably representing halogen atoms, such as trifluoromethyl, fluoro-, chloroethyl; haloalkoxy having preferably 1 to 4, particularly 1 or 2, carbon atoms and preferably 1 to 5, particularly 1 to 3, halogen atoms, the halogen atoms being identical or different and fluorine, chlorine, bromine, particularly fluorine, preferably representing halogen atoms, such as trifluoromethoxy; haloalkylthio having preferably 1 to 4, particularly 1 or 2, carbon atoms and preferably 1 to 5, particularly 1 to 3, halogen atoms, the halogen atoms being identical or different and fluorine, chlorine, bromine, particularly fluorine, preferably representing halogen atoms, such as trifluoromethylthio; alkylenedioxy having preferably 1 or 2 carbon atoms, such as methylenedioxy or ethylenedioxy; halo-substituted alkylenedioxy having preferably 1 or 2 carbon atoms and preferably 1 to 4, particularly 2 to 3, halogen atoms, the halogen atoms being identical or different and fluorine or chlorine, particularly fluorine, preferably representing halogen atoms, such as difluoromethylenedioxy, trifluoroethylenedioxy, tetrafluoroethylenedioxy; hydroxy; halogen, preferably fluorine, chlorine, bromine and iodine, particularly chlorine and bromine; cyano; nitro; amino; monoalkyl- and dialkylamino having preferably 1 to 4, particularly 1 or 2, carbon atoms per alkyl group, such as methylamino, methyl- ethylamino, n.- and i.-propylamino and methyl-n.-butylamino; formyl; carboxyl; alkylcarbonyl having preferably 2–4 carbon atoms; carbalkoxy having preferably 2 to 4, particularly 2 or 3, carbon atoms, such as carbomethoxy and carboethoxy; sulpho (—SO$_3$H); alkylsulphonyl having preferably 1 to 4, particularly 1 or 2, carbon atoms, such as methylsulphonyl and ethylsulphonyl; arylsulphonyl having preferably 6 or 10 aryl carbon atoms, such as phenylsulphonyl; phenyl, napthyl, phenoxy, naphthoxy, phenylthio, naphthylthio, which themselves can again be substituted Furthermore, R$^9$ preferably represents the radicals indicated as being preferred for R$^4$.

R$^7$ preferably represents the radicals indicated as being preferred for R$^6$, with the exception of the —NR$^8$R$^9$ and —OR$^7$ radicals.

Particularly preferred compounds of the formula I are those
in which
R$^4$ represents the —COR$^6$ radicals,
R$^6$ represents the —NR$^8$R$^9$ radicals,
R$^8$ represents hydrogen, methyl, ethyl.
R$^9$ represents phenyl which is optionally substituted by C$_1$–C$_4$-alkyl, particularly methyl, C$_1$–C$_4$-alkoxy, particularly methoxy, ethoxy, C$_1$–C$_4$-haloalkoxy, particularly trifluoromethoxy, fluorochloroethoxy, C$_1$–C$_4$-haloalkylthio, particularly trifluoromethylthio, fluorochloromethylthio, C$_1$–C$_4$-alkylthio, particularly methylthio, halosulphonyl, particularly fluorosulphonyl, chlorosulphonyl, C$_1$–C$_4$-alkylsulphonyl, particularly methylsulphonyl, C$_1$–C$_4$-haloalkylsulphonyl, particularly trifluoromethylsulphonyl, C$_1$–C$_4$-haloalkyl, particularly trifluoromethyl, methylenedioxy or ethylenedioxy, which are optionally substituted by fluorine or chlorine, halogen, particularly fluorine or chlorine, NO$_2$, phenoxy which is optionally substituted by one of the abovementioned radicals.

Very particularly preferred compounds of the formula I are those
in which
R$^4$ represents the —CONR$^8$R$^9$ radical,
R$^8$ represents hydrogen,
R$^9$ represents phenyl which is optionally substituted by halogen, particularly chlorine, NO$_2$, CF$_3$, OCF$_3$, SO$_2$F, SCF$_3$, SCF$_2$Cl, SOCF$_3$, SO$_2$CF$_3$, OCH$_3$, OCF$_2$CF$_2$H, phenoxy which is substituted by trifluoromethyl, fluoro-chloro-substituted ethylenedioxy, methyl, ethyl.

The following compounds of the formula I, in which X$^1$ represents O and R$^1$ represents phenyl and R$^2$, R$^3$, R$^4$ have the following meanings, may be mentioned individually:

| | | R$^4$ = CONR$^8$R$^9$ | |
|---|---|---|---|
| R$^2$ | R$^3$ | R$^8$ | R$^9$ |
| C$_6$H$_5$ | —CH$_3$ | H | 3-Cl, 4-CF$_3$—C$_6$H$_3$ |
| CH$_3$ | —C$_2$H$_5$ | H | 4-OCF$_2$CF$_2$H—C$_6$H$_4$ |
| —CH$_3$ | iC$_3$H$_7$ | H | 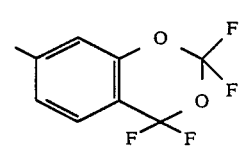 |
| —CH$_3$ | —CH$_3$ | —CH$_3$ | 4-OCF$_3$C$_6$H$_4$ |
| —C$_2$H$_5$ | —C$_2$H$_5$ | H | 4-SCF$_3$C$_6$H$_4$ |
| —CH$_3$ | —CH$_3$ | H | 3-Cl, 4-SCF$_3$—C$_6$H$_3$ |
| —C$_6$H$_5$ | —CH$_3$ | C$_2$H$_5$ | 3,4-Cl$_2$C$_6$H$_3$ |
| —CH$_3$ | —CH$_3$ | H | 4-OCF$_3$C$_6$H$_4$ |
| —CH$_3$ | —C$_2$H$_5$ | H | 4-SCF$_3$C$_6$H$_4$ |
| —C$_6$H$_5$ | —CH$_3$ | H | 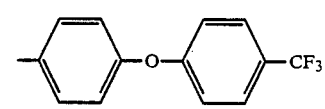 |
| —C$_6$H$_5$ | —C$_6$H$_5$ | H | 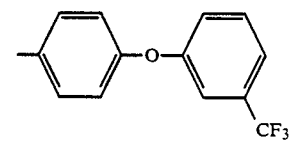 |
| —C$_6$H$_5$ | —CH$_3$ | CH$_3$ | 3-Cl, 4-CF$_3$C$_6$H$_3$ |
| —CH$_3$ | —CH$_3$ | H | 4-SCF$_3$C$_6$H$_4$ |
| —C$_6$H$_5$ | —C$_6$H$_5$ | H | 3-Cl, 4-SCF$_3$C$_6$H$_4$ |
| —4C$_6$H$_4$Cl | —CH$_3$ | H | 4-OCF$_3$—C$_6$H$_4$ |

| R² | R³ | R⁴ = CONR⁸R⁹ R⁸ | R⁹ |
|---|---|---|---|
| —CH₃ | —CH₃ | H | 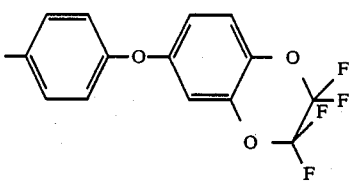 |
| —CH₃ | —iC₃H₇ | H | 3,4-(CF₃)₂—C₆H₃ |
| —CH₃ | —CH₃ | H | 3-CF₃, 4NO₂—C₆H₃ |
| —C₆H₅ | —CH₃ | H | 3-Cl, 4-SCF₂Cl—C₆H₃ |
| —CH₃ | —CH₃ | H | 3-CF₃, 4Cl—C₆H₃ |
| —C₂H₅ | —C₂H₅ | H | 3-Cl, 4-SCF₃—C₆H₃ |

The following may be mentioned as bases with which the compounds of the formula I can form salts: alkali metal and alkaline earth metal hydroxides, ammonia, primary, secondary and tertiary amines. The following bases may be particularly preferably mentioned: triethylamine, isopropylamine, t-butylamine, pyridine, picolines, trimethylamine, diisopropylamine, morpholine, morpholine, pyrrolidine, hexamethyleneimine, piperazine, N-methylpiperazine.

If 1,3-dimethyl-2-phenyl-1,3-diaza-2-phosphacyclohexane-2,4,6-trione is employed as compound of the formula II and p-bromophenylisocyanate is employed as compound of the formula III in the process 2a for the preparation of the novel cyclic malonylphosphonic diamides, then the process can be represented by the following equation:

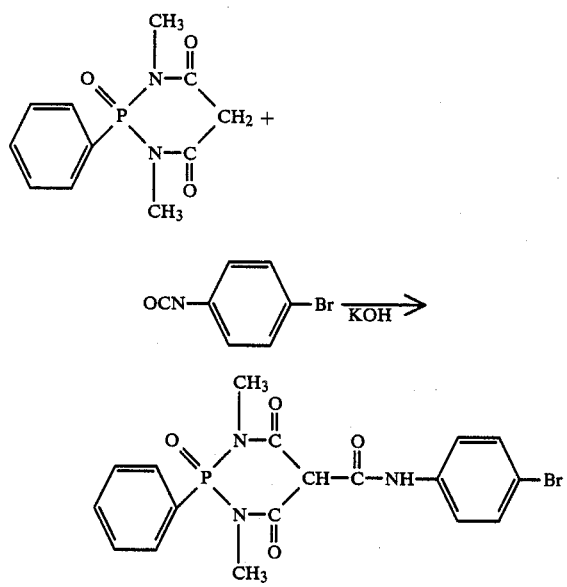

Compounds of the formula II in which the subsituents R², R³ have the preferred and particularly preferred meanings indicated for the compounds of the formula I are preferred. The following compounds of the formula II may be mentioned individually:

1,3-dimethyl-2-phenyl-1,3-diaza-2-phosphacyclohexane-2,4,6-trione, 1,3-dimethyl-2-(4-chlorophenyl)-1,3-diaza-2-phospha-cyclohexane-2,4,6-trione, 1-methyl-3-i.-propyl-2-phenyl-1,3-diaza-2-phosphacyclo-hexane-2,4,6-trione, 1,3-dimethyl-2-ethyl-1,3-diaza-phospha-cyclohexane-2,4,6-trione, 1,3-dimethyl-2-propyl-1,3-diaza-2-phospha-cyclohexane-2,4,6-trione, 1,3-dimethyl-2-i.-propyl-1,3-diaza-2-phospha-cyclohexane-2,4,6-trione, 1,3-dimethyl-2-trichloromethyl-1,3-diaza-2-phosphacyclohexane-2,4,6-trione, 1,3-dimethyl-2-(4-dimethylaminophenyl)-1,3-diaza-2-phosphacyclohexane-2,4,6-trione, 1,3-dimethyl-2-(4-nitrophenyl)-1,3-diaza-2-phospha-cyclohexane-2,4-6-trione, 1,3-diethyl-2-phenyl-1,3-diaza-2-phospha-cyclohexane-2,4,6-trione.

Isocyanates of the formula III are preferably employed in which the substituent

R⁵ represents straight-chain, branched or cyclic alkyl having up to 20 C atoms, which is optionally subtituted by halogen, particularly chlorine, fluorine, bromine, C₁-C₄-alkoxy, particularly methoxy, ethoxy, furthermore phenyl which is optionally substituted by alkyl having preferably 1 to 4, particularly 1 or 2, carbon atoms, such as methyl, ethyl, n.- and i.-propyl and n.-, i.-, s.- and t.-butyl; alkoxy having preferably 1 to 4, particularly 1 or 2, carbon atoms, such as methoxy, ethoxy, n.- and i.-propyloxy and n.-, i.-, s.- and t.-butyloxy; alkylthio having preferably 1 to 4, particularly 1 or 2, carbon atoms, such as methylthio, ethylthio, n.- and i.-propylthio and n.-, i.-, s.- and t.-butylthio; haloalkyl having preferably 1 to 4, particularly 1 or 2, carbon atoms and preferably 1 to 5, particularly 1 to 3, halogen atoms, the halogen atoms being identical or different and fluorine, chlorine or bromine, particularly fluorine, preferably representing halogen atoms, such as trifluoromethyl, fluoro-, chloroethyl; haloalkoxy having preferably 1 t 4, particularly 1 or 2, carbon atoms and preferably 1 to 5, particularly 1 to 3, halogen atoms, the halogen atoms being identical or different and fluorine, chlorine, bromine, particularly fluorine, preferably representing halogen atoms, such as trifluoromethoxy; haloalkylthio having preferably 1 to 4, particularly 1 or 2, carbon atoms and preferably 1 to 5, particularly 1 to 3, halogen atoms, the halogen atoms being identical or different and fluorine, chlorine, bromine, particularly fluorine, preferably representing halogen atoms, such as trifluoromethylthio; alkylenedioxy having preferably 1 or 2 carbon atoms, such as methylenedioxy or ethylenedioxy; halo-substituted alkylenedioxy having preferably 1 or 2 carbon atoms and preferably 1 to 4, particularly 2 to 3, halogen atoms, the halogen atoms being identical or different and fluorine or chlorine, particularly fluorine, preferably representing halogen atoms, such as difluoromethylenedioxy, trifluoroethylenedioxy, tetrafluorethylenedioxy; hydroxy; halogen, preferably fluorine, chlorine, bromine and iodine, particularly chlorine and bromine; cyano; nitro; amino; monoalkyl- and dialkylamino having preferably 1 to 4, particularly 1 or 2, carbon atoms per alkyl group, such as methylamino, methyl- ethyl-amino, n.- and i.-propylamino and methyl-n.-butylamino; formyl; carboxyl; alkylcarbonyl having preferably 2–4 carbon atoms; carbalkoxy having preferably 2 to 4, particularly 2 or 3, carbon atoms, such as carbomethoxy and carboethoxy; sulpho ($-SO_3H$); alkylsulphonyl having preferably 1 to 4, particularly 1 or 2, carbon atoms, such as methylsulphonyl and ethylsulphonyl; arylsulphonyl having preferably 6 or 10 aryl carbon atoms, such as phenylsulphonyl; phenyl, naphthyl, phenoxy, naphthoxy, phenylthio, naphthylthio, which themselves can again be substituted.

Furthermore, $R^5$ preferably represents the $-CO(S)R^{13}$ and $-COOR^{14}$ radicals, where $R^{13}$ represents phenyl which is optionally substituted by alkyl having preferably 1 to 4, particularly 1 or 2, carbon atoms, such as methyl, ethyl, n.- and i.-propyl and n.-, i.- and t.-butyl; alkoxy having preferably 1 to 4, particularly 1 or 2, carbon atoms, such as methoxy, ethoxy, n.- and i.-propyloxy and n.-, i.-, s.- and t.-butyloxy; alkylthio having preferably 1 to 4, particularly 1 or 2, carbon atoms, such as methylthio, ethylthio, n.- and i.-propylthio and n.-, i.-, s.- and t.-butylthio; haloalkyl having preferably 1 to 4, particularly 1 or 2, carbon atoms and preferably 1 to 5, particularly 1 to 3, halogen atoms, the halogen atoms being identical or different and fluorine, chlorine or bromine, particularly fluorine, preferably representing halogen atoms, suc as trifluoromethyl, fluoro-, chloroethyl; haloalkoxy having preferably 1 to 4, particularly 1 or 2, carbon atoms, preferably 1 to 5, particularly 1 to 3, halogen atoms, the halogen atoms being identical to or different and fluorine, chlorine, bromine, particularly fluorine, preferably representing halogen atoms, such as trifluoromethoxy; haloalkylthio having preferably 1 to 4, particularly 1 or 2, carbon atoms and preferably 1 to 5, particularly 1 to 3, halogen atoms, the halogen atoms being identical or different and fluorine, chlorine, bromine, particularly fluorine, preferably representing halogen atoms, such as trifluoromethylthio; alkylenedioxy having preferably 1 or 2 carbon atoms, such as methylenedioxy or ethylenedioxy; halo-substituted alkylenedioxy having preferably 1 or 2 carbon atoms and preferably 1 to 4, particularly 2 to 3, halogen atoms, the halogen atoms being identical or diffent and fluorine or chlorine, particularly fluorine, preferably representing halogen atoms, such as difluoromethylendioxy, trifluoroethylenedioxy, tetrafluoroethylenedioxy; hydroxy; halogen, preferably fluorine, chlorine, bromine and iodine, particularly chlorine and bromine; cyano; nitro; amino; monoalkyl- and dialkylamino having preferably 1 to 4, particularly 1 or 2, carbon atoms per alkyl group, such as methylamino, methyl- ethyl-amino, n.- and i.-propylamino and methyl-n.-butylamino; formyl; carboxyl; alkylcarbonyl having preferably 2–4 carbon atoms; carbalkoxy having preferably 2 to 4, particularly 2 or 3, carbon atoms, such as carbomethoxy and carboethoxy; sulpho ($-SO_3H$); alkylsulphonyl having preferably 1 to 4, particularly 1 or 2, carbon atoms, such as methylsulphonyl and ethylsulphonyl; arylsulphonyl having preferably 6 or 10 aryl carbon atoms, such as phenylsulphonyl; phenyl, naphthyl, phenoxy, naphthoxy, phenylthio, naphthylthio, which themselves can again be substituted, and where $R^{14}$ represents straight-chain, branched or cyclic alkyl having up to 20 C atoms, which is optionally substituted by halogen, particularly chlorine, fluorine, bromine, $C_1$-$C_4$-alkoxy, particularly methoxy, ethoxy, furthermore phenyl which is optionally substituted by alkyl having preferably 1 to 4, particularly 1 or 2, carbon atoms, such as methyl, ethyl, n.- and i.-propyl and n.-, i.-, s.- and t.-butyl; alkoxy having preferably 1 to 4, particularly 1 or 2, carbon atoms, such as methoxy, ethoxy, n.- and i.-propyloxy and n.-, i.-, and t.-butyloxy; alkylthio having preferably 1 to 4, particularly 1 or 2, carbon atoms, such as methylthio, ethylthio, n.- and i.-propylthio and n.-, i.-, s.- and t.-butylthio; haloalkyl having preferably 1 to 4, particularly 1 or 2, carbon atoms and preferably 1 to 5, particularly 1 to 3, halogen atoms, the halogen atoms being identical or different and fluorine, chlorine or bromine, particularly fluorine, preferably representing halogen atoms, such as trifluoromethyl, fluoro-, chloroethyl; haloalkoxy having preferably 1 to 4, particularly 1 or 2, carbon atoms, and preferably 1 to 5, particularly 1 to 3, halogen atoms, the halogen atoms being identical or different and fluorine, chlorine, bromine, particularly fluorine, preferably representing halogen atoms, such as trifluoromethoxy; haloalkylthio having preferably 1 to 4, particularly 1 or 2, carbon atoms and preferably 1 to 5, particularly 1 to 3, halogen atoms, the halogen atoms being identical or different and fluorine, chlorine, bromine, particularly fluorine, preferably representing halogen atoms, such as trifluoromethylthio; alkylenedioxy having preferably 1 or 2 carbon atoms, such as methylenedioxy or ethylenedioxy; halo-substituted alkylenedioxy having preferably 1 or 2 carbon atoms and preferably 1 to 4, particularly 2 to 3, halogen atoms, the halogen atoms being identical or different and fluorine or chlorine, particularly fluorine, preferably representing halogen atoms, such as difluoromethylenedioxy, trifluoroethylenedioxy, tetrafluoroethylenedioxy; hydroxy; halogen, preferably fluorine, chlorine, bromine and iodine, particularly chlorine and bromine; cyano; nitro; amino; monoalkyl- and dialkylamino having preferably 1 to 4, particularly 1 or 2, carbon atoms per alkyl group, such as methylamino, methyl- ethyl-amino, n.- and i.-proylamino and methyl-n.-butylamino; formyl; carboxyl; alkylcarbonyl having preferably 2–4 carbon atoms; carbalkoxy having preferably 2 to 4, particularly 2 or 3, carbon atoms, such as carbomethoxy and carboethoxy; sulpho ($-SO_3H$); alkylsulphonyl having preferably 1 to 4, particularly 1 or 2, carbon atoms, such as methylsulphonyl and ethylsulphonyl; arylsulphonyl having preferably 6 to 10 aryl carbon atoms, such as phenylsulphonyl; phenyl, naphthyl, phenoxy, naphthoxy, phenylthio, naphthylthio, which themselves can again be substituted.

Compounds of the formula IV are particularly preferably employed in which the substituent $R^{13}$ represents phenyl which is optionally substituted by $C_1$-$C_4$-alkyl, particularly methyl, $C_1$-$C_4$-alkoxy, particularly methoxy, ethoxy, $C_1$-$C_4$-haloalkoxy, particularly trifluoromethoxy, fluorochloroethoxy, $C_1$-$C_4$-haloalkylthio, particularly trifluoromethylthio, $C_1$-$C_4$-alkylthio, particularly methylthio, halosulphonyl, particularly fluorosulphonyl, chlorosulphonyl, $C_1$–$C_4$-alkylsulphonyl, particularly methylsulphonyl, $C_1$–$C_4$-haloalkylsulphonyl, particularly trifluoromethylsulphonyl, $C_1$–$C_4$-haloalkyl, particularly trifluoromethyl, methylenedioxy or ethylenedioxy, which are optionally substituted by fluorine or chlorine, halogen, particularly fluorine or chlorine, $NO_2$.

Compounds of the formula IV are very particularly preferably employed in which the substituent $R^{13}$ represents phenyl which is optionally substituted by halogen, particularly chlorine, $NO_2$, $CF_3$, $OCF_3$, $SO_2F$, $SCF_3$, $SOCF_3$, $SO_2CF_3$, $OCH_3$, $OCF_2CF_2H$, phenoxy which is substituted by trifluoromethyl, fluoro-chloro-substituted ethylenedioxy, methyl, ethyl.

Compounds of the formula IV are particularly preferably employed in which the substituent $R^{14}$ represents straight-chain, branched or cyclic alkyl having up to 6 C atoms which are optionally substituted by halogen, such as chlorine and fluorine, methoxy, ethoxy, furthermore phenyl which is optionally substituted by $C_1$–$C_4$-alkyl, particularly methyl, $C_1$–$C_4$-alkoxy, particularly methoxy, ethoxy, $C_1$–$C_4$-haloalkoxy, particularly trifluoromethoxy, fluoro-chloroethoxy, $C_1$–$C_4$-haloalkylthio, particularly trifluoromethylthio, $C_1$–$C_4$-alkylthio, particularly methylthio, halosulphonyl, particularly fluorosulphonyl, chlorosulphonyl, $C_1$–$C_4$-alkylsulphonyl, particularly methylsulphonyl, $C_1$–$C_4$-haloalkylsulphonyl, particularly trifluoromethylsulphonyl, $C_1$–$C_4$-haloalkyl, particularly trifluoromethyl, methylenedioxy or ethylenedioxy which are optionally substituted by fluorine or chlorine, halogen, particularly fluorine or chlorine.

Compounds of the formula IV are very particularly preferably employed in which the substituent $R^{14}$ represents methyl, ethyl, isopropyl, cyclohexyl, furthermore phenyl which is optionally substituted by halogen, particularly chlorine, $NO_2$, $CF_3$, $OCF_3$, $SO_2F$, $SCF_3$, $SOCF_3$, $SO_2CF_3$, $OCH_3$, $OCF_2CF_2H$ phenoxy which is substituted by trifluoromethyl, fluoro-chloro-substituted ethylenedioxy, methyl, ethyl.

The following compounds of the formula III may be mentioned individually:

4-fluorophenyl isocyanate, 4-chlorophenyl isocyanate, 3,4-dichlorophenyl isocyanate, 2-, 3- and 4-trifluoromethylphenyl isocyanate, 4-trifluoromethoxyphenyl isocyanate, 4-trifluoromethylthiophenyl isocyanate, 3-chloro-4-trifluoromethylphenyl isocyanate, 4-trifluoromethylsulphonylphenyl isocyanate, 4-tetrafluoroethoxyphenyl isocyanate, phenyl isothiocyanate, 2-, 3- and 4-chlorophenyl isothiocyanate, 2-, 3- and 4-trifluoromethylphenyl isothiocyanate, 3- and 4-Cl-benzoyl isocyanate, 3- and 4-trifluoromethylbenzoyl isocyanate, 2,6-dichloro- and 2,6-difluorobenzoyl isocyanate, benzoyl isothiocyanate, 2,6-dichloro- and 2,6-difluorobenzoyl isothiocyanate, 2-, 3- and 4-chlorophenylsulphonyl isocyanate, 4-methylphenylsulphonyl isocyanate, 3,4-dichlorophenylsulphonyl isocyanate, methoxy-, ethoxy- and isopropyloxycarbonyl isocyanate and isothiocyanate, 4-methoxy-, 4-trifluoromethoxy- and 4-trifluoromethylthiophenoxycarbonyl isocyanate and isothiocyanate.

Compounds of the formulae II and III are reacted in the presence of diluents and in the presence of bases and also, if appropriate, in the presence of further catalysts.

The following may be mentioned as bases: alkali metal, alkaline earth metal alcoholates and tertiary amines. The following bases may be particularly preferably mentioned: triethylamine, pyridine, picolines, trimethylamine, N-methylmorpholine, N-ethylpyrrolidine, diazabicyclo(4,3,0)undecene (DBU), 1,4-diazabicyclo-2,2,2-octane (DABCO), diazabicyclo(3,2,0)nonene (DBN).

All inert organic solvents are suitable as diluent. These include, in particular, aliphatic and aromatic, optionally halogenated hydrocarbons, such as pentane, hexane, heptane, cyclohexane, petroleum ether, benzine, ligroin, benzene, toluene, methylene chloride, ethylene chloride, chloroform, carbon tetrachloride, chlorobenzene and o-dichlorobenzene, furthermore ethers, such as diethyl and dibutyl ether, glycol dimethyl ether and diglycol dimethyl ether, tetrahydrofuran and dioxane, moreover ketones, such as acetone, methyl ethyl, methyl isopropyl and methyl isobutyl ketone, in addition esters, such as methyl and ethyl acetate, furthermore nitriles, such as, for example acetonitrile and propionitrile, benzonitrile, glutarodinitrile, in addition amides, such as, for example, dimethylformamide, dimethylacetamide and N-methylpyrrolidone, and also dimethyl sulphoxide, tetramethylenesulphone and hexamethylphosphoric triamide.

The catalysts which are conventional for reactions of isocyanates are suitable as catalysts. The following are suitable as catalysts: metal catalysts of Zn, Sn, Pb, such as dibutyltin dilaurate, dibutyltin dioxide, tin octoate, lead octoate, zinc octoate, zinc chloride, zinc acetate.

The reaction is carried out between 0° and 150° C., preferably between 20°–50° C. The reaction is preferably carried out under atmospheric pressure.

Compounds of the formulae II and III are employed in equimolar amounts a slight excess of one of the component brings no significant advantages.

Work-up occurs in a fashion which is known per se, for example by treatment of the reaction mixture with dilute acid, filtering off the product or separation of the organic phase and removal of the solvent by distillation.

If 1,2,3-trimethyl-1,3-diaza-2-phospha-cyclohexane-2,4,6-trione is employed as compound of the formula II and benzoyl chloride is employed as compound of the formula IV in the process 2b for the preparation of the novel cyclic malonylphosphonic diamides, then the process can be represented by the following equation:

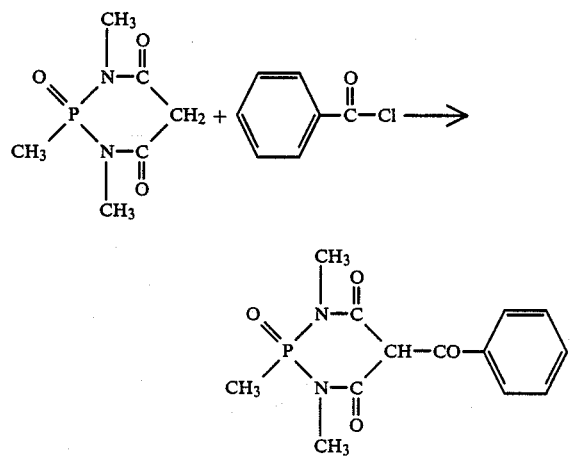

Depending on the reaction conditions, an O-acylation can also occur during this, and this can be represented by the following equation:

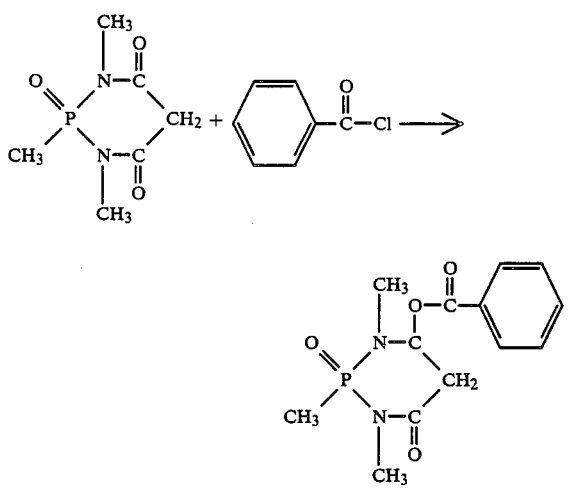

The O-acylation leads to the O-acylated compounds of the formula V specified for process 2c (compare for process 2c and process 6).

The ratio in which the C- and O-acylated compounds of the formulae I and V are produced to one another is dependent on the reaction conditions used and, particularly, on the type of base employed.

C-Acylation preferably occurs by working, at the lowest possible temperature, with alcoholic alcoholate solutions such that equivalent amounts of the alcoholate solution and of IV are added to the cooled solution of II in alcohol simultaneously and in portions.

O-Acylation preferably occurs by, for example, treating the solution of II in anhydrous pyridine with IV, and working up as conventional.

Compounds of the formulae II and IV are preferably employed in which the substituents $X^1$, $R^1$, $R^2$, $R^3$ and $R^6$ have the preferred and particularly preferred meanings mentioned for the compounds of the formula I.

The following compounds of the formula IV may be mentioned individually:

benzoyl chloride, 4-chlorobenzoyl chloride, 4-trifluoromethoxybenzoyl chloride, 4-trifluoromethylbenzoyl chloride, 2,6-dichlorobenzoyl chloride, 3-chloro-4-trifluoromethylbenzoyl chloride, 2,4,6-trimethylbenzoyl chloride, dimethylcarbamoyl chloride, N-methyl-N-phenylcarbamoyl chloride, chloroformyl piperidide, chloroformyl morpholide, N-methyl-N-(4-trifluoromethyl)phenyl-carbamoyl chloride, and methyl, ethyl, phenyl, p-chlorophenyl and p-trifluoromethyl chloroformate.

Compounds of the formulae II and IV are preferably reacted in the presence of diluents and also in the presence of acid acceptors:

The customary organic solvents are suitable as diluent. These include, in particular, aliphatic and aromatic, optionally halogenated hydrocarbons, such as pentane, hexane, heptane, cyclohexane, petroleum ether, benzine, ligroin, benzene, toluene, methylene chloride, ethylene chloride, chloroform, carbon tetrachloride, chlorobenzene and o-dichlorobenzene, furthermore ethers, such as diethyl and dibutyl ether, glycol dimethyl ether and diglycol dimethyl ether, tetrahydrofuran and dioxane, moreover ketones, such as acetone, methyl ethyl, methyl isopropyl and methyl isobutyl ketone, in addition esters, such as methyl and ethyl acetate, furthermore nitriles, such as, for example, acetonitrile and propionitrile, benzonitrile, glutarodinitrile, in addition amides, such as, for example, dimethylformamide, dimethylacetamide and N-methylpyrrolidone, and also dimethyl sulphoxide, tetramethylenesulphone and hexamethylphosphoric triamide.

The following may be mentioned as acid acceptors: alkali metal, alkaline earth metal alcoholates and tertiary amines. The following bases are particularly preferably mentioned: triethylamine, pyridine, picolines, trimethylamine, N-methyl-morpholine, N-ethyl-pyrrolidone, diazabicyclo(4,3,0)undecene (DBU), 1,4-diaza-bicyclo-2,2,2-octane (DABCO), diazabicyclo(3,2,0)nonene (DBN).

The reaction is carried out at 0°–150° C., preferably at 20°–100° C., preferably under atmospheric pressure.

The reaction is preferably carried out under a protective gas atmosphere.

The compounds of the formulae II and IV are preferably employed in equimolar ratio to one another. An excess of one or the other compound brings no significant advantage. The acid acceptors are preferably employed equimolar or in an excess of up to 10 molar, relative to the compounds of the formula III. If tertiary amines are employed as acid acceptors, these can also serve as reaction medium.

The work-up occurs in a fashion which is known per se, by filtering off the precipitated salt and concentrating the organic phase or by pouring the reaction mixture into water and concentrating the organic phase after separation.

As stated for process 2b, complete or partial O-acylation can arise during the reaction of compounds of the formula II with compounds of the formula IV. The O-acylated compounds of the formula V thereby obtained can be rearranged directly or after separation of the compounds of the formula I.

Preferred compounds of the formula V are those in which $R^{10}$ represents the —CO(S)$R^6$ radicals, $R^6$ and n having the definitions which were mentioned as being preferred and particularly preferred for the compounds of the formula I.

The following compounds of the formula V may be mentioned individually:

1,3-dimethyl-2-phenyl-4-oxybenzoyl-1,3-diaza-2-phospha-cyclohexane-2,6-dione, 1,3-dimethyl-2-phenyl-4-oxy(4-trifluoromethylbenzoyl)-1,3-diazo-2-phosphacyclohexane-2,6-dione, 1,3-dimethyl-2-phenyl-4-oxy(4-trifluoromethoxybenzoyl)-1,3-diaza-2-phosphacyclohexane-2,6-dione, 1,3-dimethyl-2-(4-chlorophenyl)-4-oxy(4-trifluoromethylthiobenzoyl)-1,3-diaza-2-phosphacyclohexane-2,6-dione, 1,2,3-trimethyl-4-oxy(4-chlorobenzyl)-1,3-diazo-2-phospha-cyclohexane-2,6-dione.

The compounds of the formula V are novel. They can also be employed directly, without further rearrangement, alone or in mixtures with the corresponding C-acylated compounds of the formula I, as active compounds for combating ecto- and endoparasites.

Process 2c is carried out by rearranging the compounds of the formula V in the presence of diluents using strong bases.

The reaction is carried out at temperatures from 0° to 150° C., preferably at 50°–100° C.

The reaction is carried out at atmospheric pressure.

4-Dimethyl- or 4-diethyl-aminopyridine preferably serve as strong bases.

The bases are added to the compounds of the formula V in the ratio 1:10, preferably 1:100.

All inert organic solvents are suitable as diluent. These include, in particular, aliphatic and aromatic, optionally halogenated hydrocarbons, such as pentane, hexane, heptane, cyclohexane, petroleum ether, benzine, ligroin, benzene, toluene, methylene chloride, ethylene chloride, chloroform, carbon tetrachloride, chlorobenzene and o-dichlorobenzene, furthermore ethers, such as diethyl and dibutyl ether, glycol dimethyl ether and diglycol dimethyl ether, tetrahydrofuran and dioxane, moreover ketones, such as acetone, methyl ethyl, methyl isopropyl and methyl isobutyl ketone, in addition esters, such as methyl and ethyl acetate, furthermore nitriles, such as, for example, acetonitrile and propionitrile, benzonitrile, glutarodinitrile, in addition amides, such as, for example, dimethylformamide, dimethylacetamide and N-methylpyrrolidone, and also dimethyl sulphoxide, tetramethylenesulphone and hexamethylphosphoric triamide.

The work-up occurs in conventional fashion: pouring into dilute acids and filtering off or separating the organic phase and subsequently concentrating.

If 1-phenyl-2-ethyl-5-carbethoxy-1,3-diaza-2-phospha-cyclohexane-2,4,6-trione is employed as compound of the formula VI and N-methyl-4-chloroaniline is employed as amine of the formula VII in process 2d, then the process can be illustrated by the following equation:

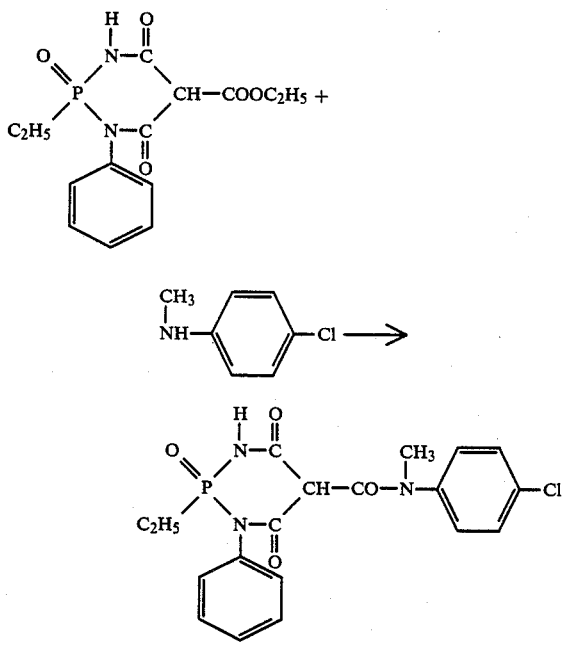

Compounds of the formula VI are novel. They are prepared as specified for process 2b. Preferred are the compounds of the formula VI in which $R^1$, $X^1$, $R^2$ and $R^3$ have the meanings mentioned as being preferred and particularly preferred for the compounds of the formula I, and in which $R^{11}$ represents methyl, ethyl, p-nitrophenyl.

The amines of the formula VII are known or can be prepared analogously to known processes.

Amines of the formula VII are preferably employed in which the substituents $R^8$ and $R^9$ have the preferred and particularly preferred meanings mentioned for the compounds of the formula I.

The following compounds of the formula VII may be mentioned individually:
4-nitroaniline, 3-chloro-4-trifluoromethylaniline, 3-trifluoromethyl-4-chloroaniline, 4-trifluoromethoxy aniline, 4-trifluoromethylmercaptoaniline, 3-chloro-4-trifluoromethoxy aniline, 3-chloro-4-trifluoromethyl-mercaptoaniline, 3-nitro-4-trifluoromethylaniline, trifluoromethyl-4-aminophenyl-sulphone, 4-(1,1,2,2-tetrafluoroethoxy)aniline, 2,6-dichloro-4-trifluoromethyl-mercapto-aniline, 4-amino-4'-trifluoromethyldiphenyl ether, 4-amino-3'-trifluoromethyl-diphenyl ether, The reaction of compounds of the formulae VI and VII preferably occurs in the presence of diluents and also in the presence of bases.

All inert organic solvents are suitable as diluent. These include, in particular, aliphatic and aromatic, optionally halogenated hydrocarbons, such as pentane, hexane, heptane, cyclohexane, petroleum ether, benzine, ligroin, benzene, toluene, methylene chloride, ethylene chloride, chloroform, carbon tetrachloride, chlorobenzene and o-dichlorobenzene, furthermore ethers, such as diethyl and dibutyl ether, glycol dimethyl ether and diglycol dimethyl ether, tetrahydrofuran and dioxane, moreover ketones, such as acetone, methyl ethyl, methyl isopropyl and methyl isobutyl ketone, in addition esters, such as methyl and ethyl acetate, furthermore nitriles, such as, for example, acetonitrile and propionitrile, benzonitrile, glutarodinitrile, in addition amides, such as, for example, dimethylformamide, dimethylacetamide and N-methylpyrrolidone, and also dimethyl sulphoxide, tetramethylenesulphone and hexamethylphosphoric triamide, furthermore alcohols, such as methanol, ethanol, propanol, butanol.

Alkali metal and alkaline earth metal hydroxides, alkali metal and alkaline earth metal alcoholates, particularly sodium methylate or ethylate, may be mentioned as bases.

The reaction is carried out between 50° and 150° C., preferably between 60°–110° C. The reaction is preferably carried out under atmospheric pressure.

The compounds of the formulae VI and VII are employed in equimolar amounts; a slight excess of one or the other component brings no significant advantages.

The work-up is carried out in a manner known per se for example by adding the reaction mixture to water, separating the organic phase and removing the solvent by distillation.

Compounds of the formula II are novel. Compounds of the formula II may preferably be mentioned in which the substituents $X^1$, $R^1$, $R^2$, $R^3$ have the preferred and particularly preferred meanings mentioned for the compounds of the formula I.

The following compounds of the formula II may be mentioned individually:
1,3-dimethyl-2-phenyl-1,3-diaza-2-phospha-cyclohexane-2,4,6-trione, 1,3-dimethyl-2-(4-chlorophenyl)-1,3-diaza-2-phospha-cyclohexane-2,4,6-trione, 1-methyl-3-i.-propyl-2-phenyl-1,3-diaza-2-phospha-cyclo-hexane-2,4,6-trione, 1,2,3-trimethyl-1,3-diaza-2-phospha-cyclohexane-2,4,6-trione, 1,3-dimethyl-2-ethyl-1,3-diaza-2-phospha-cyclohexane-2,4,6-trione, 1,3-dimethyl-2-propyl-1,3-diaza-2-phospha-cyclohexane-2,4,6-trione, 1,3-dimethyl-2-i.-propyl-1,3-diaza-2-phospha-cyclohexane-2,4,6-trione, 1,3-dimethyl-2-trichloromethyl-1,3-diaza-2-phosphacyclohexane-2,4,6-trione, 1,3-dimethyl-2-(4-dimethylaminophenyl)-1,3-diaza-2-phosphacyclohexane-2,4,6-trione, 1,3-dimethyl-2-(4-nitrophenyl)-1,3-diaza-2-phospha-cyclohexane- 2,4,6-trione, 1,3-diethyl-2-phenyl-1,3-diaza-2-phospha-cyclohexane-2,4,6-trione, 1,3-dimethyl-2-phenyl-1,3-diaza-2-phospha-cyclohexane-4,6-dione-2-thione, 1,2,3-trimethyl-2-phenyl-1,3-diaza-2-phosphacyclohexane-4,6-dione-2-thione, 1-methyl-2-phenyl-3-isopropyl-1,3-diaza-2-phospha-cyclohexane-4,6-dione-2-thione, 1,3-dimethyl-2-(4-chlorophenyl)-1,3-diaza-2-phosphacyclohexane-4,6-dione-2-thione.

If N-methyl-N'-isopropyl-phenylphosphonic diamide is employed as composed of the formula VIII and malonyl dichloride is employed as compound of the formula IX in process 4, then the course of the reaction in process 4 can be represented by the following equation:

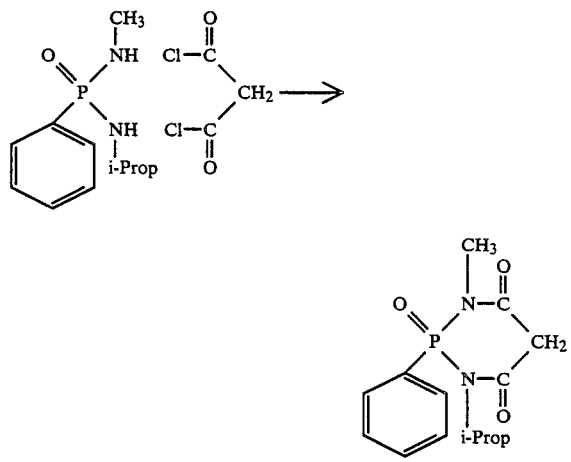

The compounds of the formulae VIII and IX are known or can be prepared analogously to known processes.

The following compounds of the formula VIII are preferably employed:
N,N'-dimethyl-phenylphosphonic diamide,
N,N'-diethyl-phenylphosphonic diamide,
N-methyl-N'-isopropyl-phenylphosphonic diamide,
N,N'-dimethyl-p-chlorophenylphosphonic diamide,
N-N'-dimethyl-p-nitrophenylphosphonic diamide,
N,N'-dimethyl-phenylthiophosphonic diamide,
N-N'-dimethyl-trichloromethylphosphonic diamide,
N-N'-dimethyl-methylphosphonic diamide,
N,N'-dimethyl-n-propylphosphonic diamide,
N,N'-dimethyl-methylthiophosphonic diamide.

The following compounds of the formula IX are preferably employed:
malonic acid, malonyl dichloride, dimethyl malonate, diethyl malonate, di-n- and di-i-propyl malonate, dibutyl malonate, diphenyl malonate.

The compounds of the formulae VIII and IX are preferably reacted in the presence of diluents and, if appropriate, in the presence of dehydrating condensation agents or catalysts.

All inert organic solvents are suitable as diluent. These include, in particular, aliphatic and aromatic, optionally halogenated hydrocarbons, such as pentane, hexane, heptane, cyclohexane, petroleum ether, benzine, ligroin, benzene, toluene, methylene chloride, ethylene chloride, chloroform, carbon tetrachloride, chlorobenzene and o-dichlorobenzene, furthermore ethers, such as diethyl and dibutyl ether, glycol dimethyl ether and diglycol dimethyl ether, tetrahydrofuran and dioxane, moreover ketones, such as acetone, methyl ethyl, methyl isopropyl and methyl isobutyl ketone, in addition esters, such as methyl and ethyl acetate, furthermore nitriles, such as, for example, acetonitrile and propionitrile, benzonitrile, glutarodinitrile, in addition amides, such as, for example, dimethylformamide, dimethylacetamide and N-methylpyrrolidone, and also dimethyl sulphoxide, tetramethylenesulphone and hexamethylphosphoric triamide.

The reaction is carried out between 0° and 150° C., preferably between 0°-110° C. The reaction is preferably carried out under atmospheric pressure.

The compounds of the formulae VIII and IX are employed in equimolar amounts; a slight excess of one or the other component brings no significant advantages.

If malonyl halides are employed as compounds of the formula IX, then the hydrohalic acid produced during the reaction is expelled by heating or flushing of inert gases.

If malonic acid is employed as compound of the formula IX, then the reaction is carried out in the presence of dehydrating condensation agents, such as, for example, carbodiimides, such as dicyclohexyl carbodiimide.

The condensation can also occur by removal of the water produced by azeotropic distillation using suitable entrainers.

If malonates are employed as compounds of the formula IX, then the reaction is carried out in the presence of alcoholates, such as, for example, alkali metal or alkaline earth metal methylate, ethylate, propylate, isopropylate, butylate, phenolate. In this case, the reaction can also be carried out in the presence of alcohols.

The compounds of the formula V are novel. Compounds of the formula V are preferably mentioned in which the substituents $X^1$, $R^1$, $R^2$, $R^3$ have the meanings preferably mentioned for the compounds of the formula I, and $R^{10}$ has the abovementioned preferred meanings. They are prepared, as mentioned above, by acylation of the compounds of the formula II and separation of the C-acylated compounds which are also produced during this [compare for process 2c (above)].

As already mentioned, the compounds of the formula V can also be employed directly, without further rearrangement to the C-acylated compounds, alone or in mixtures with the corresponding C-acylated compounds of the formula I, as active compounds for combating ecto- and endo-parasites.

The active compounds are suitable for combating animal pests, particularly insects, arachnida, nematodes, trematodes and cestodes, encountered in animal husbandry, and have favorable toxicity to warm-blooded animals. They are active against normally sensitive and resistant species and against all or some stages of development. The abovementioned pests include:

From the order of the Isopoda, for example, *Oniscus asellus, Armadillidium vulgare* and *Porcellio scaber.* From the order of the Diplopoda, for example, *Blaniulus guttulatus.* From the order of the Chilopoda, for example, *Geophilus carpophagus* and Scutigera spec. From the order of the Symphyla, for example, *Scutigerella immaculata.* From the order of the Thysanura, for example, *Lepisma saccharina.* From the order of the Collembola, for example, *Onychiurus armatus.* From the order of the Orthoptera, for example, *Blatta orientalis, Periplaneta americana, Leucophaea maderae, Blattella germanica, Acheta domesticus,* Gryllotalpa spp., *Locusta migratoria* migratorioides, *Melanoplus differentialis* and *Schistocerca gregaria.* From the order of the Dermaptera, for example, *Forficula auricularia.* From the order of the Isoptera, for example, Reticulitermes spp.. From the order of the Anoplura, for example, *Phylloxera vastatrix*, Pemphigus spp., *Pediculus humanus* corporis, Haematopinus spp. and Linognathus spp. From the order of the Mallophaga, for example, Trichodectes spp. and Damalinea spp.

From the order of the Thysanoptera, for example, *Hercinothrips femoralis* and *Thrips tabaci*. From the order of the Heteroptera, for example, Eurygaster spp., *Dysdercus intermedius, Piesma quadrata, Cimex lectularius, Rhodnius prolixus* and Triatoma spp. From the order of the Homoptera, for example, *Aleurodes brassicae, Bemisia tabaci, Trialeurodes vaporariorum, Aphis gossypii, Brevicoryne brassicae, Cryptomyzus ribis, Doralis fabae, Doralis pomo, Eriosoma lanigerum, Hyalopterus arundinis, Macrosiphum avenae,* Myzus spp., *Phorodon humili, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp. From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp. *Bucculatrix thurberiella, Phyllocnistis citrella,* Agrotis spp., Euxoa spp., Feltia spp., *Earias insulana,* Heliothlis spp., *Laphygma exigua, Mamestra brassicae, Panolis flammea, Prodenia litura,* Spodoptera spp., *Trichoplusia ni, Caprocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decem-lineata, Phaedon cochleariae,* Diabrotica spp., *Psylliodes chrysocephala, Epilachna varivestis,* Atomaria spp., *Oryzaephilus surinamensis,* Anthomonus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides, Tribolium* spp., *Tenebrio molitor,* Agriotes spp., Conoderus spp., *Melolontha melolontha, Amphimallon solstitialis* and *Costelytra zealandica.* From the order of the Hyemoptera, for example, Diprion spp., Hoplocampa spp., Lasius spp., *Monomorium pharaonis* and Vespa spp. From the order of the Diptera, for example, Aedes spp., Anopheles spp., Culex spp., Simulium spp., *Drosophila melanogaster,* Musca spp., Lyperosia spp., Fannia spp., *Calliphora erythrocephala,* Lucilia spp., Chrysomyia spp., Cuterebra spp., Gastrophilus spp., Hyppobosca spp., Stomoxys spp., Melophagus spp., Oestrus spp., Hypoderma spp., Dermatobia, Tabanus spp., Tannia spp., *Bibio hortulanus, Oscinella frit,* Phorbia spp., *Pegomyia hyoscyami, Ceratitis capitata, Dacus oleae* and *Tipula paludosa.*

From the order of the Siphonaptera, for example, *Xenopsylla cheopis* and Ceratophyllus spp, Ctenocaphalides spp., Echidnophaga. From the order of the Arachnida, for example, *Scorpio maurus* and *Latrodectus mactans.*

From the order of the Acarina, for example, *Acarus siro,* Argas spp., Obobius spec., Ornithodoros spp., Dermanyssus gallinae, Bdellonyssus spp., *Eriophyes ribis, Phyllocoptruta oleivora,* Boophilus spp., Rhipicephalus spp., Amblyomma spp., Hyalomma spp., Ixodes spp., Haemaphysalis spp., Dermacentor spp., Psoroptes spp., Chorioptes spp., Sarcoptes spp., Demodex spp., Psorergates spp., Myobia spp., Myocoptis spp., Notoedres spp., Octodectes spp., Varroa spp., Tarsonemus spp., *Bryobia praetiosa,* Panonychus spp. and Tetranychus spp.

From the order of the Pseudophyllidea, for example Diphyllobothrium spp., Spirometra spp., Schistocephalus spp., Ligula spp., Bothridium spp., Diplogonoporus spp..

From the order of the Cyclophyllidea, for example Mesocestodes spp., Anoplocephala spp., Paranoplocephala spp., Monieazia spp., Thysanosoma Spp., Thysaniezia spp., Avitellina spp., Stilesia spp., Cittotaenia spp., Anhydra spp., Bertiella spp., Taenia spp., Echinococcus spp., Hydatigera spp., Davainea spp., Raillietina spp., Humenolepis spp., Echinolepis spp., Echinocotyle spp., Diorchis spp., Dipylidium spp., Joyeuxiella spp., Diplopylidium spp..

From the subclass of the Monogenea, for example Gyrodactylus spp., Dactylogyrus spp., Polystoma spp..

From the subclass of the Digenea, for example Diplostomun spp., Posthodiplostomun spp., Schistosoma spp., Trichobilharzia spp., Ornithobilharzia spp., Austrobilharzia spp., Gigantobilharzia spp., Leucochloridium spp., Brachylaima spp., Echinostoma spp., Echinoparyphium spp., Echinochasmus spp., Hypoderaeum spp., Fasciola spp., Fasciolides spp., Fasciolopsis spp., Cyclocoelum spp., Typholocoelum spp., Paramphistomum spp., Calicophoron spp., Calicophoron spp., Cotylophoron spp., Gigantocotyle spp., Fischoederius spp. Gastrothylacus spp., Notocotylus spp., Catatropis spp., Plagiorchis spp., Prosthogonimus spp., Dicrocoelium spp., Eurytrema spp., Troglotrema spp., Paragonimus spp., Collyriclum spp., Nanophyetus spp., Opisthorchis spp., Clonorchis spp., Metorchis spp., Heterophyes spp., Metagonimus spp.. From the order of the Enoplida, for example Trichuris spp., Capillaria spp., Trichomosoides spp., Trichinella spp..

From the order of the Rhabditida, for example Micronema spp., Strongyloides spp..

From the order of the Strongylida, for example Strongylus spp., Triodontophorus spp., Oesophagodontus spp., Trichonema spp., Gyalocephus spp., Cylindropharynx spp., Poteriostomum spp., Cyclicocerus spp., Cylicostephanus spp., Oesophagostomum spp., Chabertia spp., Stephanurus spp., Ancylostoma spp., Uncinaria spp., Bunostomum spp., Globocephalus spp., Syngamus spp., Cyathostoma spp., Metastrongylus spp., Dictyocaulus spp., Muellerius spp., Protostrongylus spp., Neostrongylus spp., Cystocaulus spp., Pneumostrongylus spp., Spicocaulus spp., Elaphostrongylus spp., Parelaphostrongylus spp., Crenosoma spp., Paracrenosoma spp., Angiostrongylus spp., Aelurostrongylus spp., Filaroides spp., Parafilaroides spp., Trichostrongylus spp., Haemonchus spp., Ostertagia spp., Marshallagia spp., Cooperia spp., Nematodirus spp., Hyostrongylus spp., Obeliscoides spp., Amidostomum spp., Ollulanus spp..

From the order of the Oxyurida, for example Oxyuris spp., Enterobius spp., Passalurus spp., Syphacia spp., Aspiculuris spp., Heterakis spp.

From the order of the Ascaridida, for example Ascaris spp., Toxascaris spp., Toxocara spp., Parascaris spp., Anisakis spp., Ascaridia spp..

From the order of Spirurida, for example Gnathostoma spp., Physaloptera spp., Thelazia spp., Gongylonema spp., Habronema spp., Parabronema spp., Draschia spp., Dracunculus spp..

From the order of the Filariida, for example Stephanofilaria spp., Parafilaria spp., Setaria spp., Loa spp., Dirofilaria spp., Litomosoides spp., Brugia spp., Wuchereria spp., Onchocerca spp..

From the order of the Gigantrhynchida, for example Filicollis spp., Moniliformis spp., Macracanthorhynchus spp., Prosthenorchis spp..

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and furthermore in formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolys products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in their commercially available formulations and in the use forms, prepared from these formulations, as a mixture with other active compounds, such as insecticides. The insecticides include, for example, phosphates, carbamates, carboxylates, chlorinated hydrocarbons, phenylureas, substances produced by microorganisms.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The compounds are employed in a customary manner appropriate for the use forms.

The active compounds according to the invention are also suitable for combating arthropods which infest agricultural productive livestock such as, for example, cattle, sheep, goats, horses, pigs, donkeys, camels, buffalo, rabbits, chickens, turkeys, ducks, geese and bees, other pets, such as, for example, dogs, cats, cage birds and aquarium fish, and also so-called test animals, such as, for example, hamsters, guinea pigs, rats and mice, and finally they are also suitable for the treatment of human-pathogenic arthropods.

The active compounds according to the invention can be used prophylactically and also therapeutically for combating such arthropods. By combating these anthropods cases of death and reductions in productivity (for meat, milk, wool, hides, eggs, honey etc) should be diminished, so that more economic animal husbandry is possible by use of the active compounds according to the invention.

The active compounds according to the invention are used in the veterinary sector in a known manner by enteral administration in the form of, for example, tablets, capsules, potions, drenches, granules, pastes, boli, the feed-through process and suppositories, by parenteral administration, such as, for example, by injections (intramuscular, subcutaneous, intravenous, intraperitoneal etc), implants, by nasal administration, by dermal use in the form, for example, of dipping or bathing, spraying, pouring on and spotting on, washing and powdering, and also with the aid of moulded articles containing the active compound, such as neckbands, ear marks, tail marks, limb bands, halters, marking devices, etc.

The active compounds according to the invention are broadly active against endoparasites. They act, above all, against nematodes, especially stomach and intestine nematodes of the ruminants. In addition, they are active against such stomach and intestine nematodes which are resistant to the customary benzimidazole anthelmintic agents and can thus no longer be treated adequately.

The action was examined in animal experiments after oral, parenteral and dermal administration to test animals heavily infested with parasites. The dosages used were tolerated very well by the test animals.

The active compounds according to the invention can be used as anthelmintic agents both in human medicine and in veterinary medicine.

The active compounds according to the invention can be administered together with other customary anthelmintic agents.

The active compounds according to the invention can be used either as such or in combination with pharmaceutically acceptable excipients. Possible forms of administration in combination with various inert excipients are tablets, capsules, granules, aqueous suspensions, injectable solutions, emulsions and suspensions, elixirs, syrup, pastes and the like. Excipients of this type include solid diluents or fillers, a sterile, aqueous medium and various non-toxic organic solvents and the like. The tablets and the like envisaged for oral administration can, of course, be provided with added sweetener and the like. In the abovementioned case, the therapeutically active compound should be present in a concentration of about 0.5 to 90% by weight of total mixture, that is to say in amounts which are sufficient to achieve the abovementioned dosage range.

The formulations are prepared in a known manner, for example by extending the active compounds with solvents and/or excipients, optionally with the use of emulsifiers and/or dispersing agents, and, for example when using water as a diluent, organic solvents can optionally be used as auxiliary solvents.

Examples of auxiliary substances which may be mentioned are: water, non-toxic organic solvents, such as paraffins (for example petroleum fractions), vegetable oils (for example groundnut (sesame oil), alcohols (for example ethyl alcohol and glycerol), glycols (for example propylene glycol and polyethylene glycol) and water; solid excipients, such as, for example, natural rock powders (for example kaolins, clays, talc and chalk), synthetic rock powders (for example highly disperse silicic acid and silicates) and sugars (for example cane sugar, lactose and glucose); emulsifiers, such as non-ionic and anionic emulsifiers (for example polyoxyethylene fatty acid esters, polyoxyethylene fatty alcohol ethers, alkylsulphonates and arylsulphonates), dispersing agents (for example methylcellulose, starch and polyvinylpyrrolidone) and lubricants (for example magnesium stearate, talc, stearic acid and sodium lauryl sulphate.

In the case of oral use, the tablets can, of course, also contain, in addition to the excipients mentioned, additives such as sodium citrate, calcium carbonate and dicalcium phosphate, together with various additional substances, such as starch, preferably potato starch, gelatin and the like. Furthermore, lubricants, such as magnesium stearate, sodium lauryl sulphate and talc, can be co-used when making tablets.

In the case of aqueous suspensions and/or elixirs which are intended for oral use, the active compounds can be mixed with various flavor-improving agents or colorants in addition to the abovementioned auxiliary substances.

In the case of parenteral use, solutions, coated tablets, ampoules and the like can also be used in the form of dosage units, each dosage unit being adjusted so that it yields a single dose of the active constituent.

The active compounds according to the invention can also be present in the formulations in mixtures with other known active compounds which are used for the treatment of infections and/or sicknesses in veterinary and/or human medicine, in particular L-2,3,5,6-tetrahydro-6-phenylimidazothiazole, benzimidazole carbamates, Praziquantel and Febantel.

The active compounds can be used in customary manner. Administration is preferably effected orally, but parenteral, particularly subcutaneous, and also dermal applications (pour-on, spot-on) are possible.

In general, it has proved advantageous to administer amounts of the active compounds of about 1 to about 100 mg per kg of body weight daily to achieve effective results.

Nevertheless, it can at times be necessary to deviate from the amounts mentioned, and in particular to do so as a function of the body weight of the test animal and of the nature of the administration method, but also because of the species of animal and its individual behaviour towards the medicament, and the nature of the formulation of the medicament and the time or interval over which the administration takes place. Thus, it can be sufficient, in some cases, to manage with less than the abovementioned minimum amount, whilst in other cases the upper limit mentioned must be exceeded. Where relatively large amounts are administered, it can be advisable to divide these into several individual administrations over the course of the day. The same dosage range is envisaged for administration in human medicine and in veterinary medicine. The general sense of the other above statements also applies.

EXAMPLE A

In vitro nematode test

Caenorhabditis elegans

The active compound is dissolved in water or dimethyl sulphoxide (DMSO) and diluted in water to the desired concentration. 0.01 ml of this solution was poured onto a replica plate. 2 ml of an *E. coli* suspension to which 10–20 female animals or larvae of *Caenorhabditis elegans* in 0.5 ml of sterile M9 buffer solution had been added were introduced onto the plate. The *E. coli* suspension was prepared by adding 1.8 l of sterile M9 buffer solution to 300 ml of an overnight culture of a uracil-dependent *E. coli* strain.

The test batch was incubated for 7 days at 22° C. and then evaluated. The extent to which the active compound impairs multiplication was evaluated, and the concentration, in μg per ml, at which multiplication is inhibited by 95% is given (minimum effective dose). The following results were obtained:

| Active compound Example No. | Minimum effective dose μg/ml |
|---|---|
| 1 | 10 |
| 2 | 10 |
| 4 | 10 |
| 5 | 10 |
| 6 | 1 |
| 7 | 10 |
| 8 | 10 |
| 10 | 10 |
| 11 | 10 |
| 13 | 10 |
| 14 | 10 |
| 15 | 10 |
| 16 | 10 |
| 17 | 10 |

-continued

| Active compound Example No. | Minimum effective dose μg/ml |
|---|---|
| 18 | 10 |
| 19 | 10 |
| 20 | 10 |
| 21 | 1 |
| 22 | 10 |
| 23 | 10 |
| 24 | 1 |
| 26 | 10 |
| 27 | 10 |
| 28 | 10 |
| 31 | 100 |
| 32 | 10 |
| 33 | 10 |

EXAMPLE B

*Haemonchus contortus*/sheep

Sheep experimentally infected with *Haemonchus contortus* were treated after the end of the pre-patency time of the parasites. The active compounds were administered orally as pure active compound in gelatin capsules.

The degree of effectiveness is determined by quantitatively counting the worm eggs excreted with the faeces, before and after treatment.

Complete cessation of the excretion of eggs after the treatment means that the worms have been expelled or are so severely damaged that they can no longer produce any eggs (effective dose).

Tested active compounds and effective dosages (minimum effective dose) can be seen from the table below:

TABLE b

| *Haemonchus contortus*/sheep | |
|---|---|
| Active compound Example No. | Minimum effective dose in mg/kg |
| 22 | 10 |

EXAMPLE C

In vivo nematode test

*Strongyloides ratti*

Rats which have been experimentally infected with *Strongyloides ratti* are treated orally using a probang on three successive days 7 days after the infection. The animals are killed 13 days after the infection and the number of parasites determined. The active compound concentration is given at which at least 95% of the parasites were killed (minimum effective dose):

| Active compound Example No. | Minimum effective dose mg/kg |
|---|---|
| 16 | 5 |
| 17 | 10 |
| 19 | 25 |
| 20 | 25 |
| 21 | 10 |
| 22 | 25 |
| 23 | 50 |
| 25 | 50 |
| 26 | 25 |

EXAMPLES (a) General procedure for the preparation of compounds of the formula I according to process 2a 0.03 mol of each of the compounds II and the isocyanate (III) are initially introduced into 120 ml of dry THF and treated with a solution of 0.033 mol of "DBU" in 30 ml of THF at room temperature within 10 minutes. A slight evolution of heat occurs during this. The mixture is subsequently stirred under reflux until complete reaction has occurred (about 4-5 h) and cooled, and the entire batch is stirred into 400 ml of 10% strength hydrochloric acid. The solid which deposits during this is filtered off under suction, washed with water and dried.

(b) General procedure for the preparation of compounds of the formula I according to process 2b 0.05 mol of the compound II and 0.05 mol of "DBU" are initially introduced into 100 ml of toluene, and 0.05 mol of an acid chloride (compound IV) is added dropwise at room temperature in 10 minutes. The mixture is then stirred for 2 hours at room temperature until complete reaction has occurred, and the entire batch is stirred into 300 ml of 10% strength hydrochloric acid. The organic phase is dried over $Na_2SO_4$ and concentrated. Depending on the acylation reagent, the desired compound I contains various amounts of O-acylated compound V, which can be separated off by chromatography. The mixture of C- and O-acylated compound can also be converted directly to the desired compound I by process c.

(c) General procedure for the preparation of the compounds of the formula I according to process 2c 0.05 mol of the compound V or 0.05 mol of a mixture of C- and O-acylated compound (I and V) obtained by process b in 100 ml of toluene is treated with 0.5 g of 4-N,N-dimethyl-aminopyridine at room temperature and refluxed with stirring for 5 hours. The mixture is then cooled and stirred with 300 ml of 10% strength hydrochloric acid, the organic phase is separated off and dried over sodium sulphate. After removal of the solvent by distillation in vacuo, the residue is chromatographed or recrystallized.

(d) General procedure for the preparation of the compounds of the formula I according to process 2d 0.03 mol of the compound VI and 0.03 mol of the amine VII are suspended in 100 ml of toluene and heated at the reflux temperature for about 10 hours under nitrogen, ethanol being evolved. The reaction mixture is cooled and the solid is filtered off. The product filtered off is rinsed with ethanol and subsequently dried.

(e) General procedure for the preparation of the compounds of the formula II according to process 4

0.11 mol of malonyl chloride is added dropwise to 0.1 mol of phosphonic diamide VIII in 100 ml of dry methylene chloride in about 30 minutes at 5° C. with external cooling. The mixture is then stirred for 2-4 hours at 40° C. and cooled, and the reaction batch is filtered. The filtrate is concentrated to dryness by removal of the solvent by distillation in vacuo and the residue is recrystallized from ethanol/petroleum ether.

The compounds of the following table are obtained according to one of the processes (a)-(d) specified above:

$$\begin{array}{c} R^2\ O \\ | \quad \| \\ X^1 \quad N-C \\ \diagdown \quad | \quad \diagdown \\ P \quad CH-C-NH-\bigcirc-Y \\ \diagup \quad | \quad \| \\ R^1 \quad N-C \quad O \\ | \quad \| \\ R^3\ O \end{array} \qquad I$$

| Ex. | $X^1$ | $R^1$ | $R^2$ | $R^3$ | Y | M.p. °C. |
|---|---|---|---|---|---|---|
| 1 | S | Phenyl | $CH_3$ | $CH_3$ | 3-$CF_3$ | 108–111 |
| 2 | S | Phenyl | $CH_3$ | $CH_3$ | 3-Cl | 118–120 |
| 3 | S | Phenyl | i-$C_3H_7$ | i-$C_3H_7$ | 3-Cl | 181–182 |
| 4 | S | Phenyl | $CH_3$ | $CH_3$ | 3-$CF_3$, 4-Cl | Oil |
| 5 | S | Phenyl | $CH_3$ | $CH_3$ | 4-$SCF_3$ | Oil |
| 6 | S | Phenyl | $CH_3$ | $CH_3$ | 4-$CF_3$ | 130–131 |
| 7 | S | Phenyl | $CH_3$ | $CH_3$ | 3,4-$(CF_3)_2$ | amorph |
| 8 | S | Phenyl | $CH_3$ | $CH_3$ | 3-Cl, 4-$SCF_2Cl$ | >200 |
| 9 | S | Phenyl | $CH_3$ | $CH_3$ | 4(—O—C$_6$H$_4$—$CF_3$) | 54 |
| 10 | S | Phenyl | $CH_3$ | $CH_3$ | 3-$CF_3$, 4-$NO_2$ | 65 |
| 11 | O | Phenyl | $CH_3$ | i-$C_3H_7$ | 3-Cl | 158–162 |
| 12 | S | Phenyl | $CH_3$ | i-$C_3H_7$ | 3-Cl | 144–147 |
| 13 | O | Phenyl | $CH_3$ | $CH_3$ | 4-$OCF_3$ | 131-2 |
| 14 | O | Phenyl | $CH_3$ | $CH_3$ | 4-$SCF_3$ | 131-2 |
| 15 | O | Phenyl | $CH_3$ | $CH_3$ | 4-$CF_3$ | 149-50 |
| 16 | O | Phenyl | $CH_3$ | $CH_3$ | 3-Cl, 4-$OCF_3$ | 116-18 |
| 17 | O | Phenyl | $CH_3$ | $CH_3$ | 3-Cl, 4-$SCF_3$ | 116-18 |
| 18 | O | Phenyl | $CH_3$ | $CH_3$ | 3,4 $Cl_2$ | 168–169 |
| 19 | O | 4-Chlor-Phenyl | $CH_3$ | $CH_3$ | 4-$CF_3$ | 130–134 |
| 20 | O | 4-Chlor-Phenyl | $CH_3$ | $CH_3$ | 4-$SCF_3$ | 85–88 |
| 21 | O | 4-Chlor-Phenyl | $CH_3$ | $CH_3$ | 4-$OCF_3$ | 132–134 |
| 22 | O | Phenyl | $CH_3$ | $CH_3$ | 4-Cl | 133–141 |
| 23 | O | Phenyl | $CH_3$ | $CH_3$ | 3-$CF_3$, 4-Cl | 138–143 |
| 24 | O | Phenyl | $CH_3$ | $CH_3$ | 3-Cl | 151–153 |
| 25 | O | Phenyl | $CH_3$ | $CH_3$ | 4(—O—C$_6$H$_4$—$CF_3$) | 164–166 |
| 26 | O | $CH_3$— | $CH_3$— | $CH_3$— | 4-$SCF_3$ | 182–184 |
| 27 | O | $CH_3$— | $CH_3$— | $CH_3$— | 4-$OCF_3$ | 171–174 |
| 28 | O | $CH_3$— | $CH_3$— | $CH_3$— | 4-$CF_3$ | 183–186 |
| 29 | O | n$C_3H_7$ | $CH_3$— | $CH_3$— | 4-$SCF_3$ | 243 |
| 30 | O | n$C_3H_7$ | $CH_3$— | $CH_3$— | 3-$CF_3$, 4-Cl | 137 |
| 31 | O | n$C_3H_7$ | $CH_3$— | $CH_3$— | 4-$CF_3$ | 156 |
| 32 | O | $CH_3$— | $CH_3$— | $CH_3$— | 4(—O—C$_6$H$_4$—$CF_3$) | 135–140 |
| 33 | O | $CH_3$— | $CH_3$— | $CH_3$— | 3-Cl, 4-$CF_3$ | 138–140 |

It is understood that the specification and examples are illustrative but not limitative of the present invention and that other embodiments within the spirit and scope of the invention will suggest themselves to those skilled in the art.

We claim:
1. A cyclic malonylphosphonic diamide of the formula

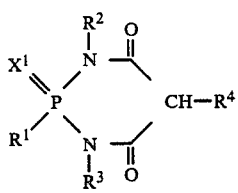

in which
X¹ represents O or S,
R¹ represents $C_{1-3}$-alkyl, phenyl, naphthyl, phenyl or naphthyl substituted by alkyl having 1 to 4 carbon atoms, alkoxy having 1 to 4 carbon atoms, alkylthio having 1 to 4 carbon atoms, haloalkyl having 1 to 4 carbon atoms and 1 to 5 halogen atoms, haloalkoxy having 1 to 4 carbon atoms and 1 to 5 halogen atoms, haloalkylthio having 1 to 4 carbon atoms and 1 to 5 halogen atoms, hydroxy, halogen, cyano, nitro, amino, monoalkyl- and dialkylamino having 1 to 4 carbon atoms per alkyl group, formyl, carboxyl, alkylcarbonyl having 2-4 carbon atoms, carbalkoxy having 2 to 4 carbon atoms, sulpho(—SO₃H), alkylsulphonyl having 1 to 4 carbon atoms, arylsulphonyl having 6 or 19 aryl carbon atoms, and/or phenyl, naphthyl, phenoxy, naphthoxy, phenylthio or naphthylthio,
R² represents hydrogen, $C_1$-$C_4$-alkyl, phenyl or benzyl,
R³ represents hydrogen, $C_1$-$C_4$-alkyl, phenyl or benzyl,
R⁴ represents the —COR⁷, —CSR⁷ —COOR⁷, —CSOR⁷, —CONR⁸R⁹ or —CSNR⁸R⁹ radical,
R⁷ represents straight-chain, branched or cyclic alkyl having up to 20C atoms, straight-chain, branched or cyclic alkyl having up to 20C atoms and substituted by halogen, $C_1$-$C_4$-alkoxy, phenyl, phenyl which is substituted by alkyl having 1 to 4 carbon atoms, alkoxy having 1 to 4 carbon atoms, alkylthio having 1 to 4 carbon atoms and 1 to 5 halogen atoms, haloalkoxy having 1 to 4 carbon atoms and 1 to 5 halogen atoms, haloalkylthio having 1 to 4 carbon atoms and 1 to 5 halogen atoms, alkylenedioxy having 1 or 2 carbon atoms, halo-substituted alkylenedioxy having one or 2 carbon atoms and 1 to 4 halogen atoms, hydroxy, halogen, cyano, nitro, amino, monoalkyl- and dialkylamino having 1 to 4 carbon atoms per alkyl group, formyl, carboxyl, alkylcarbonyl having 2-4 carbon atoms, carbalkoxy having 2 to 4 carbon atoms, sulpho(—SO₃H), alkylsulphonyl having 1 to 4 carbon atoms, arylsulphonyl having 6 or 10 aryl carbon atoms, and/or phenyl, naphthyl, phenoxy, naphthoxy, phenylthio or naphthylthio,
R⁸ represents hydrogen or $C_{1-4}$-alkyl, and
R⁹ represents $C_{1-4}$-alkyl, phenyl, phenyl substituted by alkyl having 1 to 4 carbon atoms, alkoxy having 1 to 4 carbon atoms, alkylthio having 1 to 4 carbon atoms, haloalkyl having 1 to 4 carbon atoms and 1 to 5 halogen atoms, haloalkoxy having 1 to 4 carbon atoms and 1 to 5 halogen atoms, haloalkylthio having 1 to 4 carbon atoms and 1 to 5 halogen atoms, hydroxy, halogen, cyano, nitro, amino, monoalkyl- and dialkylamino having 1 to 4 carbon atoms per alkyl group, formyl, carboxyl, alkylcarbonyl having 2-4 carbon atoms, carbalkoxy having 2 to 4 carbon atoms, sulpho(—SO₃H), alkylsulphonyl having 1 to 4 carbon atoms, arylsulphonyl having 6 or 10 aryl carbon atoms, and/or phenyl, naphthyl, phenoxy, naphthoxy, phenylthio or naphthylthio, or —COR⁶ or —CSR⁶,
or a salt thereof.

2. A compound or salt according to claim 1, in which
X¹ represents O,
R⁴ represents the —CONR⁸R⁹ radical,
R⁸ represents hydrogen, methyl or ethyl,
R⁹ represents phenyl or phenyl substituted by $C_1$-$C_4$-alkyl, $C_1$-$C_4$-alkoxy, $C_1$-$C_4$-haloalkoxy, $C_1$-$C_4$-haloalkylthio, $C_1$-$C_4$-alkylthio, halosulphonyl, $C_1$-$C_4$-alkylsulphonyl, $C_1$-$C_4$-haloalkylsulphonyl or $C_1$-$C_4$-haloalkyl.

3. A compound or salt according to claim 1, in which
R⁴ represents the —CONR⁸R⁹ radical,
R⁸ represents hydrogen,
R⁹ represents phenyl which is optionally substituted by halogen, NO₂, CF₃, OCF₃, SO₂F, SCF₃, SCF₂Cl, SOCF₃, SO₂CF₃, OCH₃, OCF₂CF₂H, phenoxy which is substituted by trifluoromethyl, fluoro-chloro-substituted ethylenedioxy, methyl or ethyl.

4. A compound according to claim 1 wherein such compound is 1,3-dimethyl-2-phenyl-4-(4-trifluoromethoxyphenyl-carbamoyl)-1,3-diaza-2-phosphacyclohexane-2,4,6-trione of the formula

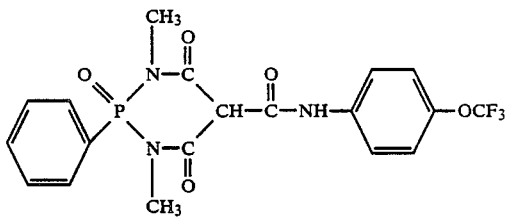

or a salt thereof.

5. A compound according to claim 1 wherein such compound is 1,3-dimethyl-2-phenyl-4-(4-trifluoromethylthiophenyl-carbamoyl)-1,3-diaza-2-phosphacyclohexane-2,4,6-trione of the formula

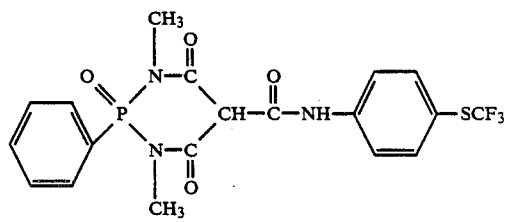

or a salt thereof.

6. A compound according to claim 1 wherein such compound is 1,3-dimethyl-2-phenyl-4-(3-chloro-4-trifluoromethoxyphenylcarbamoyl)-1,3-diaza-2-phosphacyclohexane-2,4,6-trione of the formula

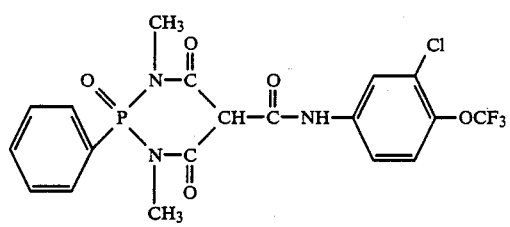

or a salt thereof.

7. A compound according to claim 1 wherein such compound is 1,3-dimethyl-2-(4-chlorophenyl)-4-trifluoromethoxyphenylcarbamoyl)-1,3-diaza-2-phospha-cyclohexane-2,4,6-trione of the formula

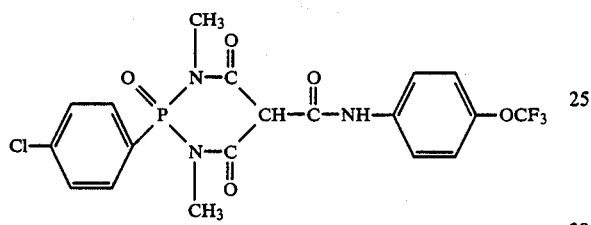

or a salt thereof.

8. A compound according to claim 1 wherein such compound is 1,3-dimethyl-2-phenyl-4-(4-chlorophenyl-carbamoyl)-1,3-diaza-2-phospha-cyclohexane-2,4,6-trione of the formula

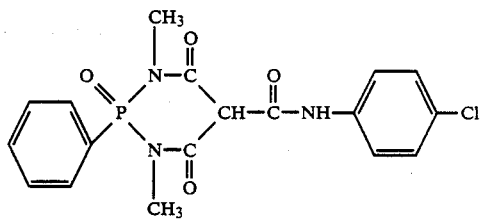

or a salt thereof.

9. A pesticidal composition comprising a pesticidally effective amount of a compound or salt according to claim 1 and a diluent.

10. A method of combating pests which comprises applying to such pests or to a pest habitat a pesticidally effective amount of a compound or salt according to claim 1.

11. The method according to claim 10 wherein such compound is
1,3-dimethyl-2-phenyl-4-(4-trifluoromethoxyphenyl-carbamoyl)-1,3-diaza-2-phospha-cyclohexane-2,4,6-trione,
1,3-dimethyl-2-phenyl-4-(4-trifluoromethylthio-phenylcarbamoyl)-1,3-diaza-2-phospha-cyclohexane-2,4,6-trione,
1,3-dimethyl-2-phenyl-4-(3-chloro-4-trifluoromethoxyphenyl-carbamoyl)-1,3-diaza-2-phospha-cyclohexane-2,4,6-trione,
1,3-dimethyl-2-(4-chlorophenyl)-4-trifluoromethoxyphenyl-carbamoyl)-1,3-diaza-2-phospha-cyclohexane-2,4,6-trione or
1,3-dimethyl-2-phenyl-4-(4-chlorophenyl-carbamoyl)-1,3-diaza-2-phospha-cyclohexane-2,4,6-trione,
or a salt thereof.

* * * * *

UNITED STATES PATENT AND TRADEMARK OFFICE
CERTIFICATE OF CORRECTION

PATENT NO. : 4,804,655

DATED : Feb. 14, 1989

INVENTOR(S) : Müller et al.

It is certified that error appears in the above-identified patent and that said Letters Patent is hereby corrected as shown below:

| | |
|---|---|
| Title Page, under "Abstract", line 2 after formula | Delete "Xrepresents" and substitute $--X^1$ represents-- |
| Col. 3, line 53 | Insert --5.-- before "The" |
| Col. 4, line 55 | Delete "t" in second instance and substitute --to-- |
| Col. 4, line 62 | Delete "to" in second instance and substitute --or-- |
| Col. 9, line 25 | Delete "morpholine" |
| Col. 10, line 49 | Delete "t" and substitute --to-- |

Signed and Sealed this

Ninth Day of January, 1990

Attest:

JEFFREY M. SAMUELS

*Attesting Officer*     *Acting Commissioner of Patents and Trademarks*